United States Patent [19]

Ito et al.

[11] Patent Number: 5,379,769
[45] Date of Patent: Jan. 10, 1995

[54] ULTRASONIC DIAGNOSTIC APPARATUS FOR DISPLAYING AN IMAGE IN A THREE-DIMENSIONAL IMAGE AND IN A REAL TIME IMAGE AND A DISPLAY METHOD THEREOF

[75] Inventors: Yukio Ito, Matsudo; Yoshihiro Goto, Tokyo, both of Japan

[73] Assignee: Hitachi Medical Corporation, Tokyo, Japan

[21] Appl. No.: 158,226

[22] Filed: Nov. 29, 1993

[30] Foreign Application Priority Data

Nov. 30, 1992 [JP] Japan .................................. 4-340951
Dec. 2, 1992 [JP] Japan .................................. 4-345136

[51] Int. Cl.⁶ .......................... A61B 8/00; A61B 8/06
[52] U.S. Cl. ......................... 128/660.07; 128/660.05; 128/661.09; 128/916
[58] Field of Search ................. 128/660.07, 661.09, 128/660.04–660.05, 916

[56] References Cited

U.S. PATENT DOCUMENTS

5,078,195 1/1992 Furuhata ........................ 128/916 X
5,152,292 10/1992 Karp ........................... 128/661.09 X Primary Examiner—Francis Jaworski
Attorney, Agent, or Firm—Antonelli, Terry, Stout & Kraus

[57] ABSTRACT

An ultrasonic diagnostic apparatus includes a circuit for detecting a portion which changes more than a predetermined magnitude in the received echo signal, the portion being a changing point corresponding to a measurement point to be measured within the inspected object, a circuit for measuring an elapsed time until the changing point is detected from a timing point at which the echo signal is detected, a circuit for obtaining luminance values in correspondence with the elapsed time as display luminance values of the measurement point, and a circuit for displaying the measurement point within the inspected object by the luminance values thus obtained.

16 Claims, 9 Drawing Sheets

ULTRASONIC DIAGNOSTIC APPARATUS FOR DISPLAYING AN IMAGE IN A THREE-DIMENSIONAL IMAGE AND IN A REAL TIME IMAGE AND A DISPLAY METHOD THEREOF

BACKGROUND OF THE INVENTION

The present invention relates to an ultrasonic diagnostic apparatus for obtaining a B-mode image of a diagnostic portion of an inspected object by utilizing ultrasonic waves and, more particularly, to a method of displaying measured information of the diagnostic portion in a three-dimensional image and in a real time and an ultrasonic diagnostic apparatus using such display method.

A conventional ultrasonic diagnostic apparatus includes a transducer unit for transmitting and receiving ultrasonic waves to and from an inspected object, an ultrasonic wave transmission and reception unit for driving the transducer unit to generate ultrasonic waves and processing a reflected echo signal received, a B-mode image making circuit for receiving the reflected echo signal from the ultrasonic wave transmission and reception unit and digitizing the input reflected echo signal to make a B-mode image of the diagnostic object, an image display unit for converting image data from the B-mode image making circuit into an analog signal to thereby display an image, and a control circuit for controlling the above-mentioned respective elements. When the ultrasonic wave image of the diagnostic object of the inspected object is displayed in a three-dimensional image by such conventional ultrasonic diagnostic apparatus, the B-mode scanning done by the transmitted ultrasonic wave is sequentially moved in the direction perpendicular to the B-mode scanning surface by using the transducer unit of a three-dimensional scanning to thereby collect a number of B-mode image in a three-dimensional measurement space. A number of collected B-mode images are supplied to an image processing apparatus other than the above-mentioned ultrasonic diagnostic apparatus. Then, this image processing apparatus forms and displays the above-mentioned B-mode images as a three-dimensional image by reconstructing the three-dimensional image according to a Voxel method or the like. Also, in an ultrasonic diagnostic apparatus which has a function to display a bloodstream, for example, in color, a number of color Doppler images in the three-dimensional measurement space are collected, and a number of color Doppler images thus collected are supplied to the image processing apparatus similarly as described above, in which they are formed as a three-dimensional image by effecting the three-dimensional image reconstruction.

However, in such conventional ultrasonic diagnostic apparatus, a number of B-mode images in the three-dimensional measurement space are temporarily collected. Then, a number of B-mode images thus collected are supplied to the image processing apparatus other than the ultrasonic diagnostic apparatus, in which they are displayed as the three-dimensional image by effecting the three-dimensional image reconstruction and then displayed. Therefore, a three-dimensional image cannot be displayed in a real time while the diagnostic object of the inspected object is being scanned by the ultrasonic wave beams. Thus, the three-dimensional shape of the above-mentioned diagnostic object cannot be observed statically or dynamically so that sufficient diagnostic information cannot be obtained.

SUMMARY OF THE INVENTION

Therefore, in view of the aforesaid problems, it is an object of the present invention to provide an ultrasonic diagnostic apparatus which can display measurement information of a diagnostic object in a three-dimensional image and in a real time.

1. In order to attain the aforesaid objects, according to the ultrasonic diagnostic apparatus of the present invention, when a black and white picture is displayed, each echo signals received are processed in a three-dimensional processing and making a voxel which has a three-dimensional information and these voxels are sequentially displayed as pictures, thereby making it possible to effect the three-dimensional display in a real time.

In the three-dimensional processing in this case, high frequency noise is reduced from the received signal by using a low-pass filter and a signal from the human body surface to a constant depth is eliminated. Thereafter, the above-mentioned signal is differentiated by a differentiation circuit to detect a portion in which the level of the differentiated signal is changed by a predetermined magnitude, i.e., a changing point corresponding to a measurement point to be detected within the inspected object, thereby measuring an elapsed time required until the changing point in the signal appears from the echo signal was received. Then, a distance from the body surface to the measurement point is calculated by obtaining a product of this elapsed time and the velocity of sound of the ultrasonic wave. Thus, since a position of a viewpoint of observer and a position of the measurement point are made clear, in advance a black and white image is displayed in a three-dimensional image with reference to a table in which position information of a previously-prepared viewpoint, a distance to the measurement point and a corresponding relationship with respect to luminance values which are changed in response to the distance are registered while changing the luminance value of the detected measurement point.

2. When a color image of a moving inspected object is displayed, at least two ultrasonic wave beams or more are transmitted in the same direction and a Doppler frequency shift, signal is extracted from the received echo signal. Each Doppler frequency shift signal is processed in a three-dimensional image and sequentially displayed as images, thereby to make it possible to effect the three-dimensional display in a real time.

In the three-dimensional processing in this case, the Doppler frequency shift signal is extracted from the received echo signal by a circuit which detects a motion by effectively utilizing a Doppler effect. Then, a portion in which the level of the extracted Doppler frequency shift is changed by a predetermined magnitude, i.e., a changing point corresponding to a measurement point to be detected within the inspected object is detected, thereby measuring an elapsed time required until the changing point in the signal appears from the echo signal was received. Then, a distance from the body surface to the measurement point is calculated by obtaining a product of this elapsed time and the velocity of sound of the ultrasonic wave. Thus, since a position of a viewpoint of observer and a position of the measurement point are made clear, a black and white image is displayed in a three-dimensional image with reference to a table in which position information of a previously-prepared viewpoint, a distance to the measurement point and a corresponding relationship with respect to luminance values which are changed in response to the distance are registered while changing the luminance value of the detected measurement point.

In the case of the three-dimensional display, moving portions are displayed in different colors depending on the direction that the moving portions approach or retreat the ultrasonic wave beam transmitting direction.

Since the present invention is arranged as described above, measurement information of the diagnostic object of the inspected object can be displayed in a three-dimensional image in a real time. Therefore, a three-dimensional shape of the above-mentioned diagnostic object can be observed statically or dynamically. In particular, this invention is effective that description of internal organs such as a heart or the like and a moving object display thereof can be made in a three-dimensional image in a real time.

DESCRIPTION OF THE PREFERRED EMBODIMENTS

Figure 1:
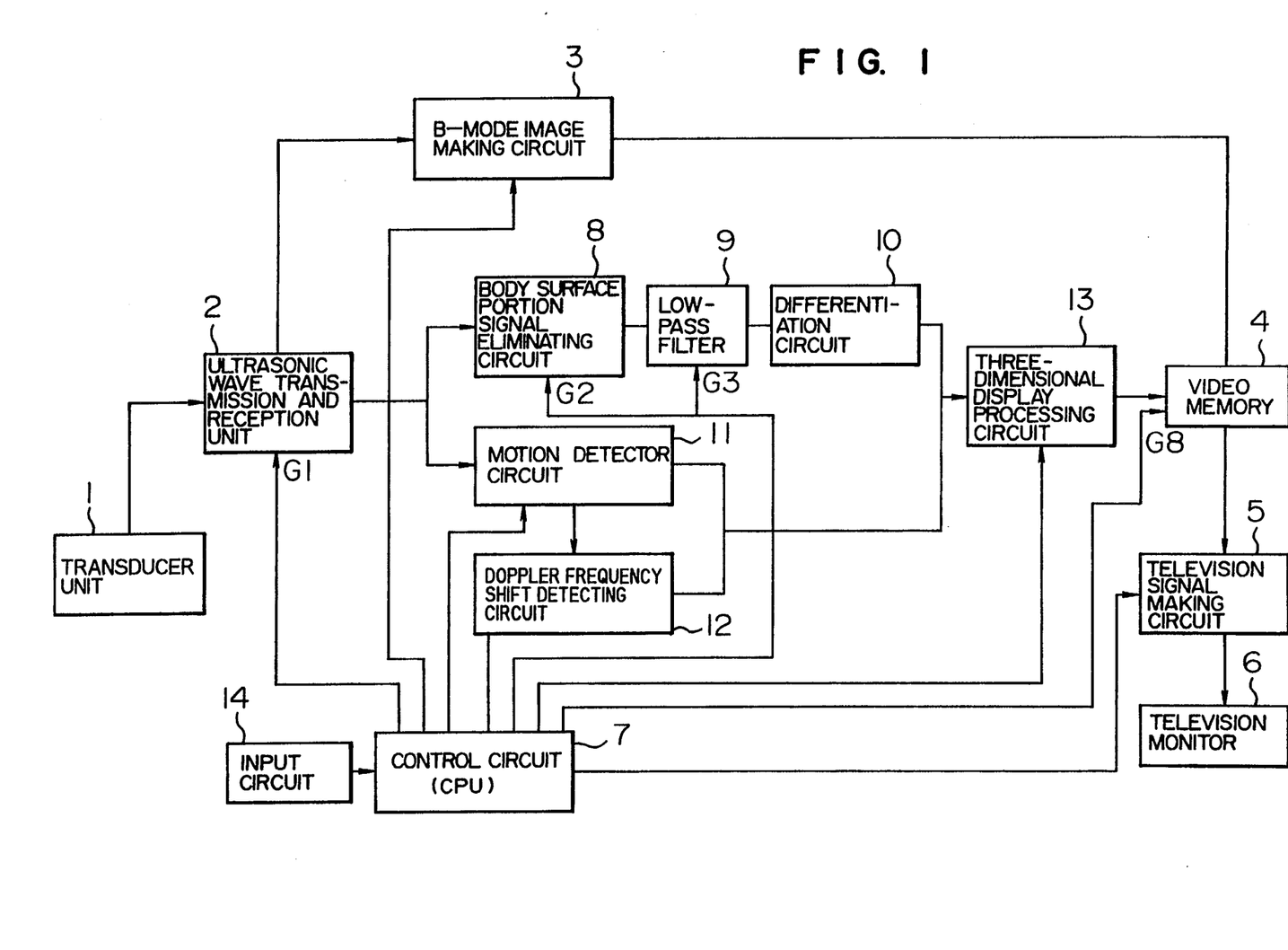
FIG. 1 is a block diagram showing an ultrasonic diagnostic apparatus according to an embodiment of the present invention.

FIG. 1 is a block diagram showing an ultrasonic diagnostic apparatus according to an embodiment of the present invention. This ultrasonic diagnostic apparatus can obtain a B-mode image of a diagnostic portion of an inspected object by effectively utilizing ultrasonic waves and can also display a three-dimensional image.

As shown in FIG. 1, the ultrasonic diagnostic apparatus comprises a transducer unit 1, an ultrasonic wave reception unit 2, a B-mode image making unit 3, a video memory 4, a television signal making circuit 5, a television monitor 6 and a control circuit 7. This ultrasonic diagnostic apparatus further comprises a body surface portion signal eliminating circuit 8, a low-pass filter 9, a differentiation circuit 10, a motion detecting circuit 11, a Doppler frequency shift detecting circuit 12, a three-dimensional display processing circuit 13, and an input circuit 14.

The transducer unit 1 is adapted to transmit or receive ultrasonic waves to and from an inspected object by mechanically or electronically carrying out the linear scanning, sector scanning or the like. The transducer unit 1 incorporates therein a vibrator for generating ultrasonic waves and which also receives a reflected echo signal, though not shown. Incidentally, the transducer unit 1 according to the present invention is adapted to obtain measurement information of a three-dimensional measurement space when being sequentially moved in the direction perpendicular to the B-mode scanning surface while carrying out the linear scanning, for example. The ultrasonic wave reception unit 2 generates ultrasonic waves by driving the transducer unit 1 and also processes a received reflected echo signal. The ultrasonic wave reception unit 2 incorporates therein a pulser for transmitting a driving pulse to the transducer unit 1 and a pre-amplifier for amplifying the reflected echo signal that is received by the transducer unit 1, though not shown. The B-mode image making circuit converts an input reflected echo signal supplied thereto from the ultrasonic wave reception unit 2 into a digital signal to thereby make a black and while B-mode image (i.e., tomography image) of the diagnostic object.

The video memory 4 is supplied with data representative of the black and white B-mode image thus formed and makes and stores therein an ultrasonic wave image of each slice image. The video memory 4 has a storage capacity of several 10s of frames, for example.

The television signal making circuit 5 converts input data representing the ultrasonic wave image read out thereto from the video memory 4 into a television signal (analog video signal) that can be displayed as an image. Further, the television monitor 6 is supplied with the television signal from the television signal making circuit 5 and displays an ultrasonic wave image. The video memory 4, the television signal making circuit 5 and the television monitor 6 constitute an image display unit.

The control circuit 7 is adapted to control operation of the above-mentioned circuit elements. The control circuit 7 is formed of a CPU (central processing unit), for example, and transmits control signals to the above-mentioned respective circuit elements. An input circuit 14 connected to the control circuit 7 is supplied with control information that are used to control the above-mentioned circuit elements. The control information thus input is supplied to the above-mentioned control circuit 7.

The body surface portion signal eliminating circuit 8, the low-pass filter 9 and the differentiation circuit 10 are utilized when an object is displayed in a three-dimensional image in a real time. The body surface portion signal eliminating circuit 8 is adapted to eliminate a signal part of less than a predetermined depth from the body surface from the reflected echo signal input thereto from the ultrasonic wave reception unit 2. The body surface portion signal eliminating circuit 8 eliminates a signal part of less than a predetermined depth by switching the input reflected echo signal and a zero-level signal in accordance with a control signal G2 representing a threshold value input thereto from the input circuit 14 through the control circuit 14. The low-pass filter 9 is adapted to reduce high frequency noise from the reflected echo signal output from the above-mentioned body surface portion signal eliminating circuit 8. A filter characteristic of the low-pass filter 9 can be set arbitrarily by a control signal G3 input thereto from the input circuit 14 through the control circuit 7. An output signal of the low-pass filter 9 is differentiated by the differentiation circuit 10 and then supplied to a three-dimensional display processing circuit 13. The three-dimensional display processing circuit 13 is adapted to detect a portion in which the level of the differentiated signal outputted from the differentiation circuit 10 is changed by a predetermined magnitude, i.e., a changing point corresponding to a measurement point to be detected within the inspected body. The measurement point is located at a predetermined depth from the body surface. Then, the three-dimensional display processing circuit 13 calculates a display luminance value in response to an elapsed time and also outputs the calculated luminance signal to the video memory 4.

Figure 2:
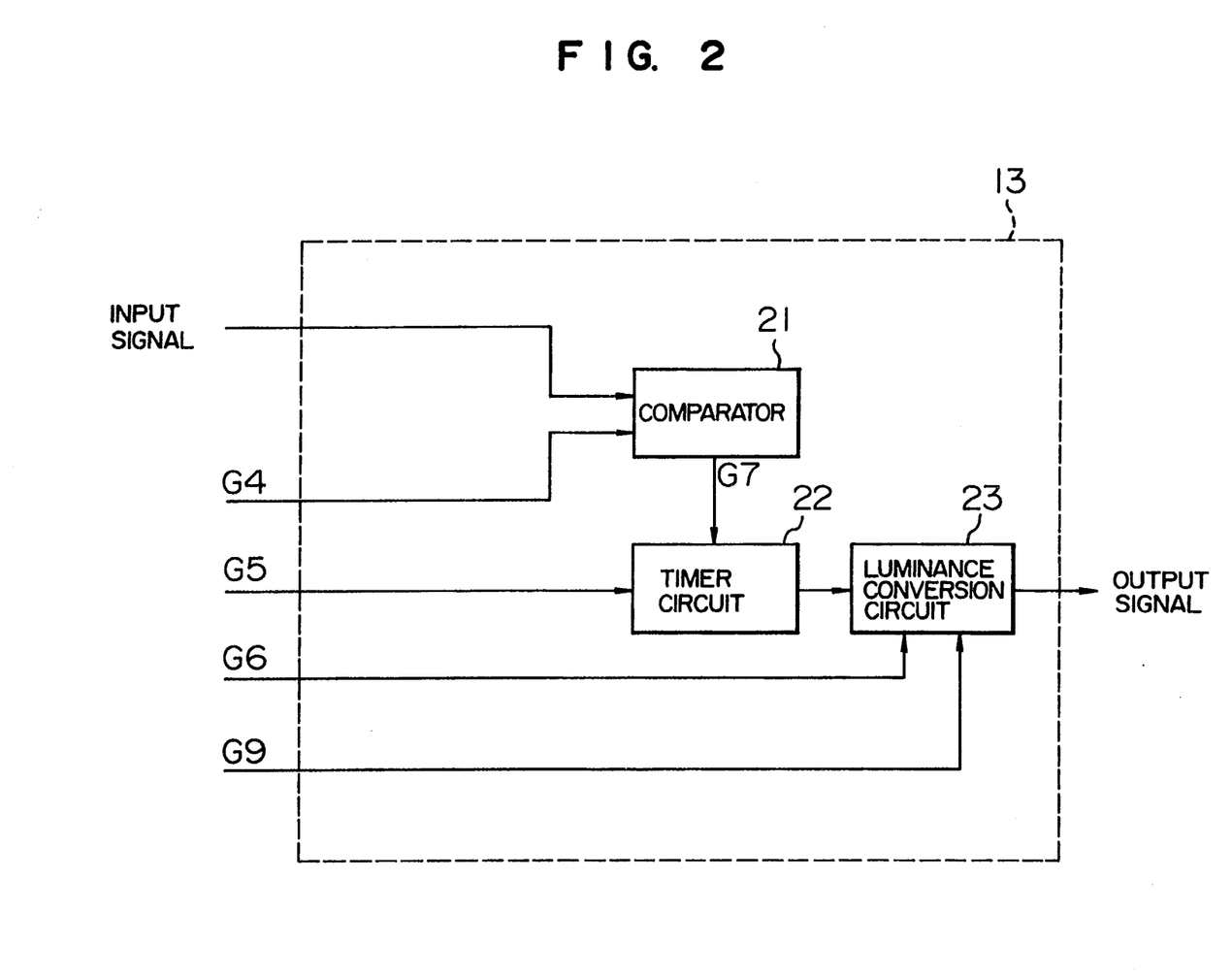
FIG. 2 is a block diagram showing an inside circuit arrangement of a three-dimensional display circuit used in the present invention.

The inside circuit arrangement of the three-dimensional display processing circuit 13 is illustrated in FIG. 2.

As shown in FIG. 2, the three-dimensional display processing circuit 13 comprises a comparator 21 for comparing the signal differentiated by the differentiation circuit 10 and a control signal G4 representing the threshold value transmitted from the input circuit 14 through the control circuit 7, a timer circuit 22 for measuring a time passed since the transducer unit 1 started to receive the reflected echo signal from the diagnostic portion on the basis of a control signal G5 input thereto from the control circuit 7, and a luminance conversion circuit 23 for calculating and outputting a luminance value displayed by the image displaying units (4, 5, 6) from the input elapsed time value measured by the timer circuit 22.

The timer circuit 22 is reset and started by the control signal G5 from the control circuit shown in FIG. 7 and then stopped by a signal G7 output thereto from the above-mentioned comparator 7 to thereby calculate the elapsed time. The luminance conversion circuit 23 is a conversion table memory in which there is registered a corresponding relationship among the elapsed time thus calculated, viewpoint position information supplied thereto by a control signal G6 from the control circuit 7, and the luminance value. The luminance conversion circuit 23 is formed of a ROM (read only memory), for example. The luminance conversion circuit 23 is not limited to the ROM and may be a high speed calculator such as a CPU for calculation and conversion.

When a moving inspected object is displayed as a color image, the ultrasonic wave beam is transmitted at least twice from the transducer unit 1 in the same direction. The scanning done by the ultrasonic wave beam is the same as that used when a black and white image is obtained. Therefore, the scanning of the ultrasonic wave beam is sequentially moved in the direction perpendicular to the scanning surface. The echo signal received by the ultrasonic wave transmission and reception unit 2 is switched by the switch 4 and then input to the motion detecting circuit 11 that is adapted to detect a moving portion of the inspected object by utilizing a Doppler effect. The motion detecting circuit 11 is comprised of a phase detector for detecting a moving inspected object and an MTI filter, etc., though not shown. The motion detecting circuit 11 outputs a Doppler frequency shift signal from at least two echo signals or more of the ultrasonic wave beams transmitted in the same direction and inputs the outputted Doppler frequency shift signals to the three-dimensional display processing circuit 13.

The Doppler frequency shift detecting circuit 12 is adapted to detect on the basis of the Doppler frequency shift signal outputted by the motion detecting circuit 11 whether the moving direction of the inspected object approaches or goes away from the transmitting direction of the ultrasonic wave beams, and then outputs a color control signal that is used to display an approaching frequency shift and a going away frequency shift in different colors. This color control signal is input to the luminance conversion circuit 23 in the three-dimensional display processing circuit 13, in which it is used to select display colors.

The three-dimensional display processing circuit 13 processes the Doppler frequency shift signal in a similar way or method used when the differentiated signal is processed. More particularly, the three-dimensional display processing circuit 13 detects by comparing the Doppler frequency shift signal with the threshold signal G4 by the comparator 21 a point (changing point) at which the change of the outputted Doppler signal becomes larger than a predetermined value. The changing point also corresponds to the measurement point to be detected within the inspected body. The timer circuit 22 is adapted to measure a time required until the above-mentioned changing point is detected since the echo signal was received. A reception of the echo signal is started immediately after the ultrasonic wave beam is transmitted. The luminance conversion circuit 23 calculates a distance from the transducer unit 1 to the measurement point on the basis of the elapsed time and the velocity of sound within the biological body and displays position information of a viewpoint of observer provided within the inside, position of measurement point and a relationship relative to the luminance value displayed in different brightness at each scanning in a three-dimensional image in a real time with reference to the registered conversion table. In that case, the going away frequency shift is displayed in blue and the approached frequency shift is displayed in red.

Figure 3:
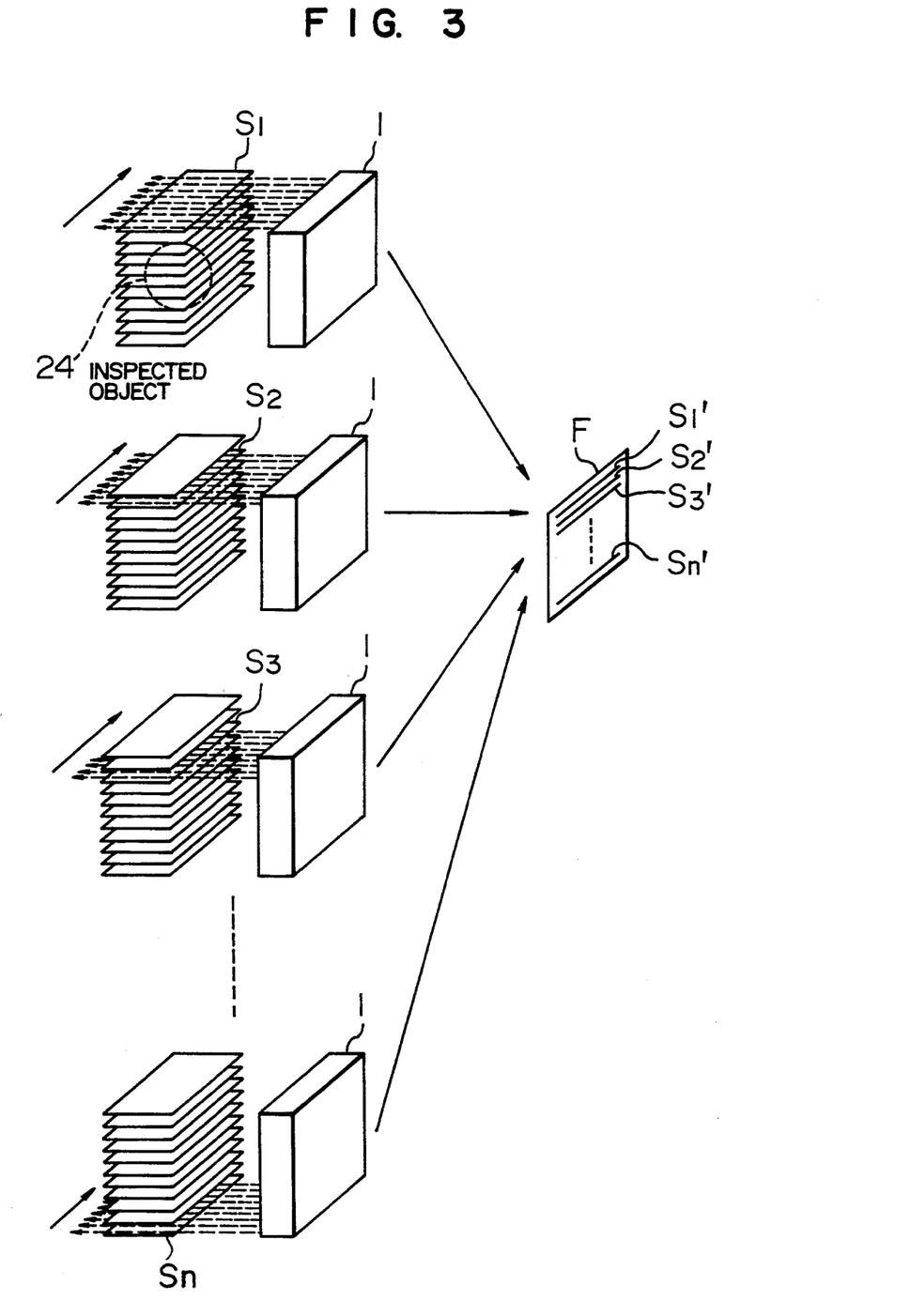
FIG. 3 is a diagram used to explain the condition that measurement information of a three-dimensional measurement space is obtained by the transmission and reception of an ultrasonic beam transmitted from a transducer unit.

The scanning operation and the display operation of the three-dimensional image in the thus arranged ultrasonic diagnostic apparatus will be described below. Initially, the ultrasonic wave transmission and reception unit 2 drives the transducer unit 1 in response to the control signal G1 from the control circuit 7 shown in FIG. 1 and also transmits and receives the ultrasonic wave from and to the inspected object by controlling the transmitting position of the ultrasonic wave beam. Then, the ultrasonic wave transmission and reception unit 2 obtains the measurement information of the three-dimensional measurement space by sequentially moving the B-mode scanning of the ultrasonic wave beam transmitted from the transducer unit 1 at a proper spacing in the direction perpendicular to the B-mode scanning surface. At that time, let us consider an organ of a spherical shape, for example, as an inspected object 24 within the inspected object and B-mode scanning surfaces that are shifted at a proper interval sequentially as $S_1, S_2, \ldots, S_n$. When the scanning for obtaining the measurement information of the three-dimensional measurement space is examined on the plane F perpendicular to each of the B-mode scanning surfaces $S_1$ to $S_n$, it is to be appreciated that such scanning is carried out as the movement of ultrasonic wave beams $S_1', S_2', \ldots, S_n'$. By such scanning, each reflected echo signal reflected from the inspected object 24 is received at the transducer unit 1, converted into an electrical signal and then processed by the ultrasonic transmission and reception unit 2 so as to become a reflected echo luminance signal.

Figure 4A:
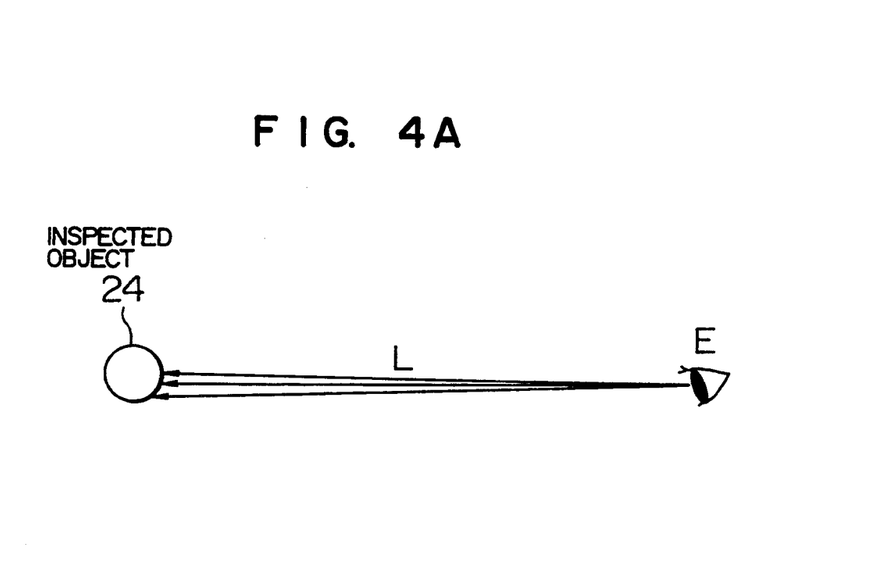
FIGS. 4A and 4B are schematic diagrams showing a principle by which an inspected object is displayed as a three-dimensional image on the basis of the measurement information respectively.

When the inspected object 24 is displayed as a three-dimensional image on the basis of the measurement information of the three-dimensional measurement space as shown in FIG. 3, the three-dimensional image is given by use of a shade difference by a difference of a distance L up to the surface of the inspected object 24 as the inspected object 24 is seen from the viewpoint E as shown in FIG. 4A. In other words, the three-dimensional image may be displayed under the condition that the brightness at each point of the inspected object 24 is varied due to the difference of the distance L. In this case, if the transducer unit 1 shown in FIG. 3 is placed between the viewpoint E and the inspected object 24 as shown in FIG. 4B, then the distance L from the viewpoint E to a surface $17_1$ of the inspected object 24 is expressed by a sum of a distance $L_1$ from the viewpoint E to a transducer unit surface P and a distance $L_2$ from the transducer unit surface P to a surface $17_2$ of the inspected object 24.

Figure 4B:
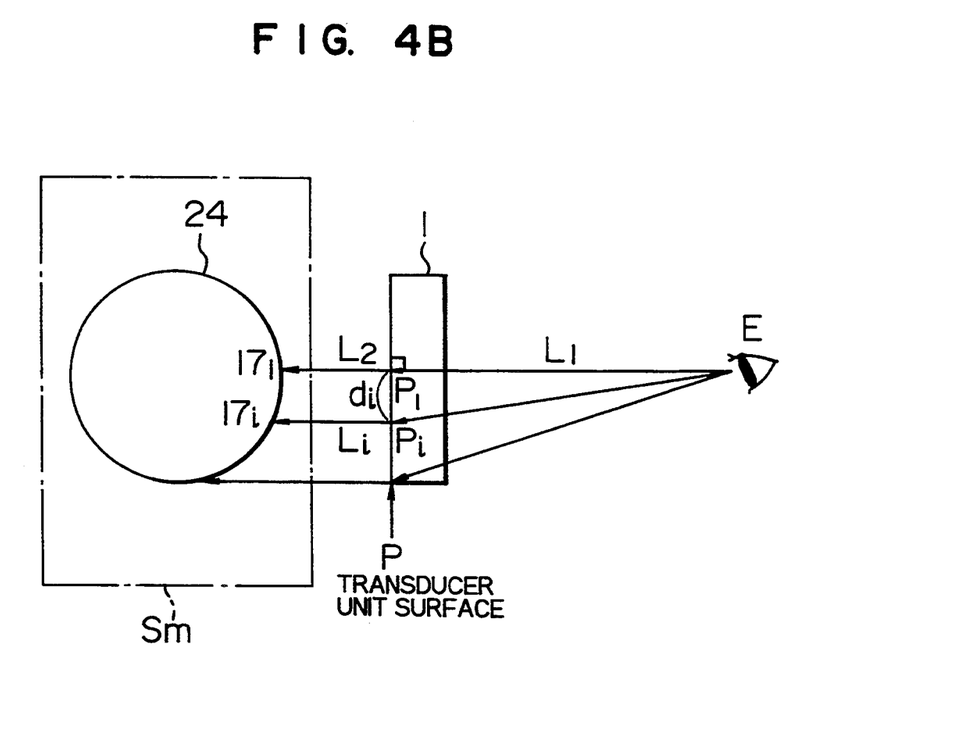
Figure 5A:
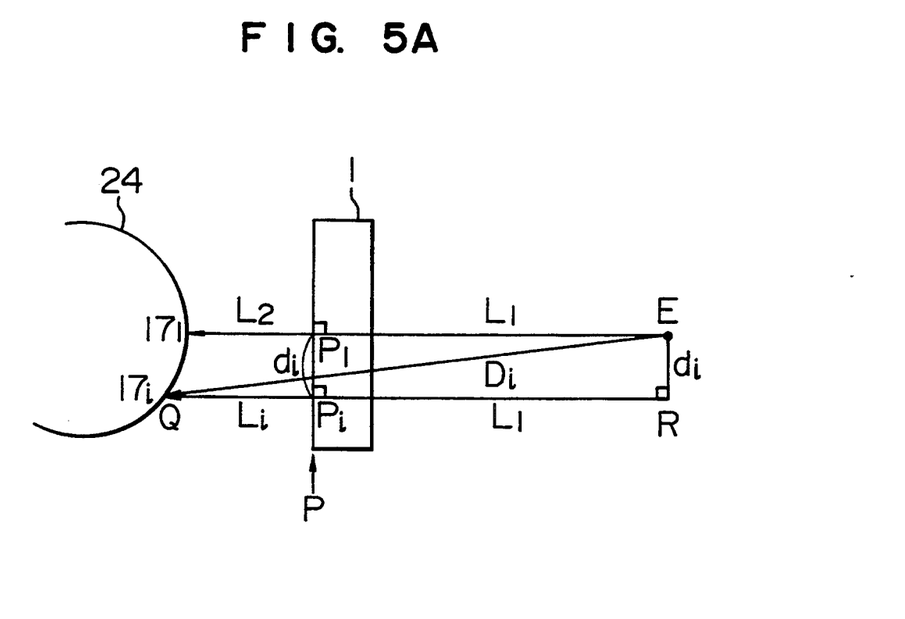
FIGS. 5A and 5B are schematic diagrams used to explain the condition that a three-dimensional image of an inspected object is displayed by rewriting the condition shown in FIG. 4B.

In FIG. 5A that is provided by rewriting FIG. 4B, assuming that Li is a distance up to a surface $17i$ of the inspected object 24 measured by the ultrasonic wave beam transmitted and received at a point Pi shifted from a transducer unit center $P_1$ by a distance di and that Di is a distance from the viewpoint E to the surface $17i$ of the inspected object 24, then the distance Di is calculated as the following equation (1) by the application of the Pythagorean theorem in a right-angled triangle $\triangle QRE$ in which the above-mentioned surface $17i$ is assumed to be a point Q:

$$Di^2 = (L_1 + Li)^2 + di^2 \qquad (1)$$

From the above-mentioned equation (1), it is to be appreciated that, if the distance Li from the transducer unit surface P to the surface $17i$ of the inspected object 24 is calculated with respect to each of ultrasonic wave beams and also the distance di from the transducer unit center $P_1$ to the ultrasonic wave beam transmitting position Pi is calculated, then the distance Di can be calculated by using the above-mentioned equation (1). Then, a brightness at each point on the inspected object 24 may be changed in response to the distance Di from the viewpoint E to the arbitrary point $17i$ on the surface of the inspected object 24. For example, a brightness is increased in the nearby point in which the distance Di is small and a brightness is decreased in the distance point in which the distance Di is large.

Figure 5B:
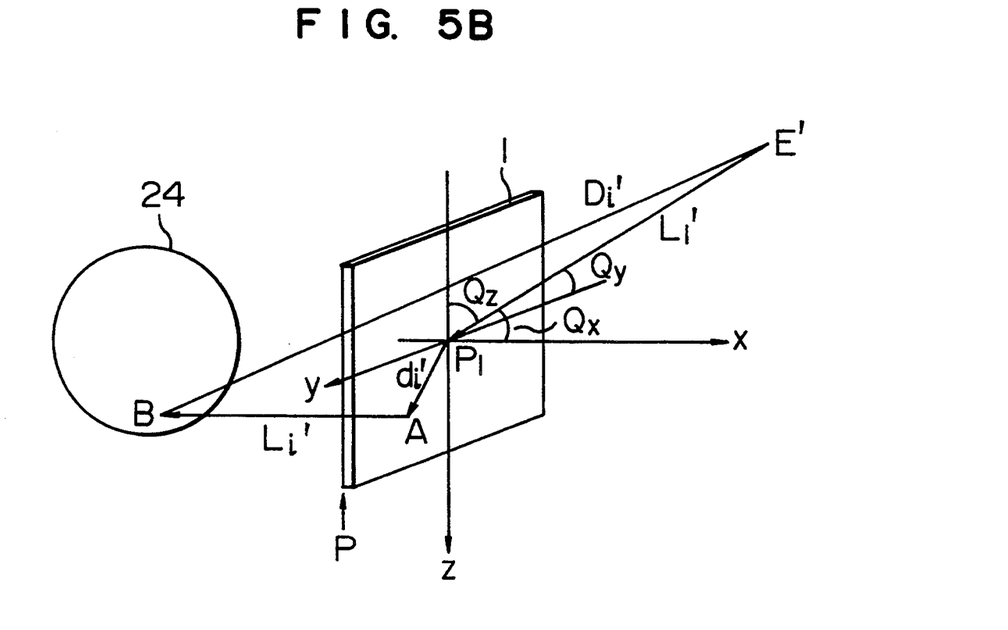

FIG. 5B shows FIG. 5A in a three-dimensional image the transducer unit center $P_1$ is assumed to be an original point, and there are provided x, y and z coordinates. Then, $\theta x$, $\theta y$ and $\theta z$ assume arbitrary angles relative to the x axis, y axis and z axis, respectively. Also E' assumes a new viewpoint that is moved when a distance from the above-mentioned original point $P_1$ is $L_1'$. With this arrangement, similarly to FIG. 5A, if the distance $L_1$, from the point A on the transducer unit surface P to the point B on the inspected object 24 is calculated with respect to each of the ultrasonic wave beams and also the distance di' from the transducer unit center $P_1$ to the above-mentioned point A is calculated, then the inspected object 24 can be displayed in a three-dimensional image. More specifically, in FIG. 5B, since the viewpoint E, the ultrasonic wave beam transmitting point A and the ultrasonic wave beam transmitting direction are already known and the distance Li' can be calculated on the basis of these elements, a distance Di' from the above-mentioned viewpoint E' to the point B on the inspected object 24 can be calculated by the following equation (2):

$$Di' = |\overrightarrow{EB}| = |\overrightarrow{EP_1} + \overrightarrow{P_1A} + \overrightarrow{AB}| \qquad (2)$$

While the viewpoint E is set to one point on the straight line relative to the transducer unit surface P in FIG. 4B and FIG. 5A as described above, the present invention is not limited thereto and the following variant is also possible. That is, in actual practice, an arbitrary point is selected to be a viewpoint in advance. Then, as shown in FIG. 5B, the distance Li' from the ultrasonic wave beam transmitting position to the surface of the inspected object 24 is measured and the distance Di' from the arbitrary viewpoint E' to the surface of the measured inspected object 24 is calculated. Then, a brightness at each point on the inspected object 24 may be varied in response to this distance Di'.

Figure 6A:
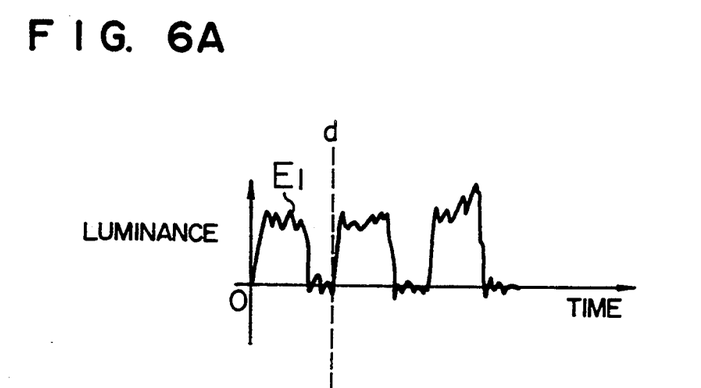
FIGS. 6A through 6D are schematic diagrams used to explain a procedure for calculating a distance from the transducer unit surface to the surface of the inspected object, respectively.
Figure 6B:
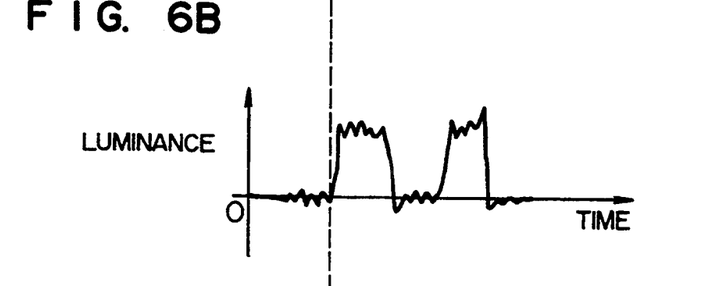
Figure 6C:
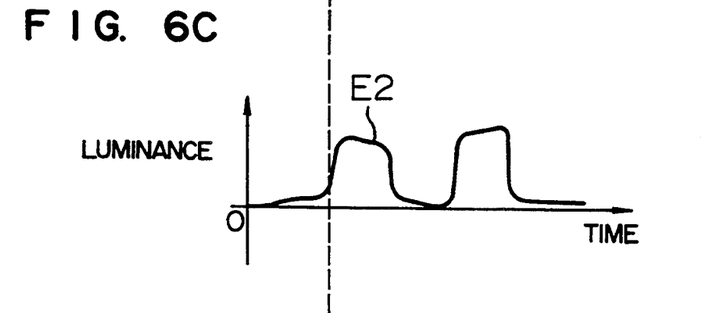

The technique for calculating the distance Li from the transducer unit surface P shown in FIGS. 4B and 5A to the surface of inspected object 24 will be described with reference to FIGS. 6A through 6D. Initially, an echo signal reflected on the surface of the inspected object 24 is received by the transducer unit 1 shown in FIG. 1 and converted into an electrical signal. Then, this electrical signal is processed by the ultrasonic wave transmission and reception unit 2 so as to become a reflection echo luminance signal as shown in FIG. 6A. This reflection echo luminance signal is input to the body surface portion signal eliminating circuit 8, in which a signal component $E_1$ of a portion (body surface portion) shallower than the body surface shown in FIG. 6A by a predetermined depth d is eliminated as shown in FIG. 6B. Thereafter, the signal from the above-mentioned body surface portion signal eliminating circuit 8 is input to the low-pass filter 9 shown in FIG. 1, in which a high frequency noise contained in the input signal is eliminated as shown in FIG. 6C. Then, the signal from the low-pass filter 9 is input to the differentiation circuit 10 which then detects a degree in which a change $E_2$ (see FIG. 6C) of signal intensity occurs due to the reflection caused at the boundary portion (see reference symbol d) at different compositions of the internal organ contained in such signal.

Figure 6D:
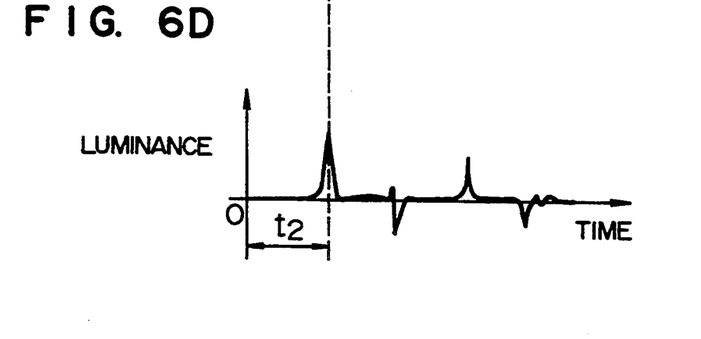

The state of the change of the reflection echo signal appears in the signal processed by the differentiation circuit 10 in the form of the amplitude, as shown in FIG. 6D. To this end, a time t2 in which the change of an arbitrary magnitude appears since the transducer unit 1 started receiving the reflection echo signal is obtained by the comparator 21 and the timer circuit 22 shown in FIG. 2. At that time, the comparator 21 compares the differentiation signal shown in FIG. 6D and the threshold value represented by the above-mentioned control signal G4. When the differentiation signal and the threshold value represented by the control signal G4 are coincident with each other or when the differentiation signal becomes larger than the threshold value, the comparator 21 supplies the signal G7 to the timer circuit 22. The timer circuit 22 starts measuring a time under the control signal G5 representing the reflection echo signal reception start time from the control circuit 7 and ends the time measurement by the input of the signal G7 from the comparator 21. Thus, as shown in FIG. 6D, the time t2 required till the time point t1 in which the change of arbitrary magnitude appears since the transducer unit 1 started receiving the reflection echo signal. In this case, if the boundary portion at the depth d is the surface of the inspected object 24 shown in FIG. 4B, then the distance Li from the transducer unit surface P to the surface of the inspected object 24 is calculated on the basis of the time t2 required until the time point t1 of such change.

A signal representing the time t2 measured by the timer circuit 22 is input to the luminance conversion circuit 23 shown in FIG. 2, and thereby converted into an image display luminance value corresponding to the magnitude of the value of the time t2 calculated by using the conversion table memory provided in the luminance conversion circuit 23, and also digitized. Incidentally, there are provided a plurality of conversion table memories at every viewpoint position and these conversion table memories are selected by the control signal G6 representative of the viewpoint position information. Then, the above-mentioned digital signal is supplied to the video memory 4 shown in FIG. 1 as the display luminance signal. Thereafter, the video memory 4 obtains position information of the ultrasonic wave beam transmission and reception on the basis of the control signal G8 supplied thereto from the control circuit 7, and records the above-mentioned digital signal on the basis of such position information.

Figure 8:
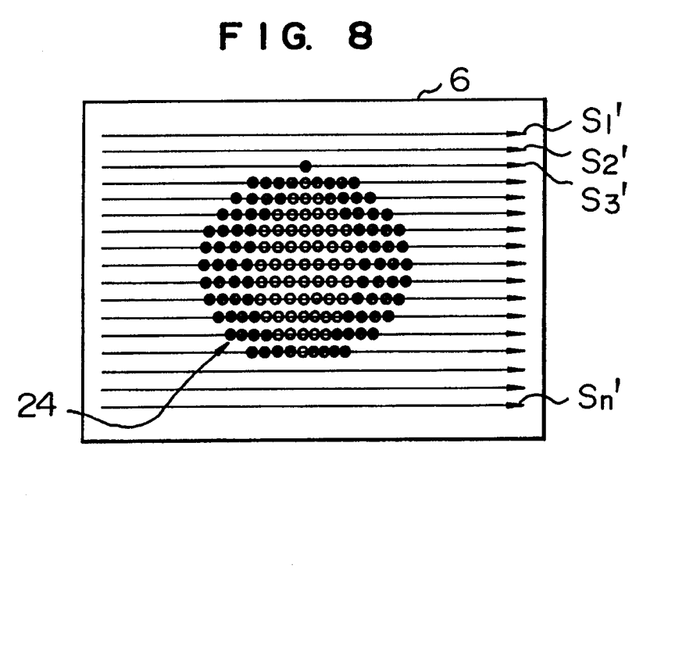
FIG. 8 is a diagram used to explain an example of a displayed three-dimensional image according to the present invention.

According no the above-mentioned operation, the distance Li from the transducer unit surface P to the surface of the inspected object 24 is calculated with respect to each of ultrasonic wave beams in a certain B-mode scanning surface Sm shown in FIG. 4B, and then converted into a luminance value corresponding to the calculated distance Li. Further, the above-mentioned distance Li is calculated with respect to the respective B-mode scanning surfaces $S_1$ to $S_n$ shown in FIG. 3 and then converted into luminance values. Thus, display luminance signals are simultaneously obtained along the moving loci of ultrasonic wave beams $S_1'$ to $S_n'$ corresponding to the sliced surfaces under the condition that the whole of the inspected object 24 of spherical shape shown in FIG. 3 is sliced, and then recorded on the above-mentioned video memory 4. Then, when such video data is displayed on the television monitor 6 through the television signal making circuit 5 shown in FIG. 1, as shown in FIG. 8, the portion in which the distance Li shown in FIG. 4B is small is displayed with large brightness and the portion in which the distance Li is large is displayed with small brightness in response to the shape of the inspected object 24. Therefore, the image data is displayed as a two-dimensional image having different brightness in accordance with the distance of the inspected object. As a consequence, the displayed image shown in FIG. 8 is observed as a three-dimensional image in which a luminance difference is expressed in accordance with the shape of the inspected object 24, thereby making it possible to grasp the shape of the inspected object or the like satisfactorily.

Figure 7A:
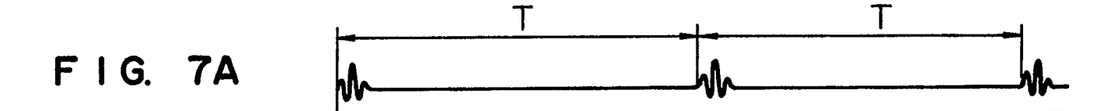
FIGS. 7A through 7D are schematic diagrams used to explain a procedure for calculating a distance from the transducer unit surface to a motion surface of the inspected object, respectively.
Figure 7B:
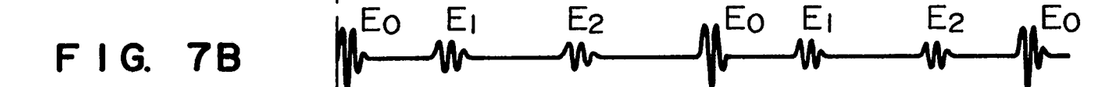
Figures 7C, 7D:
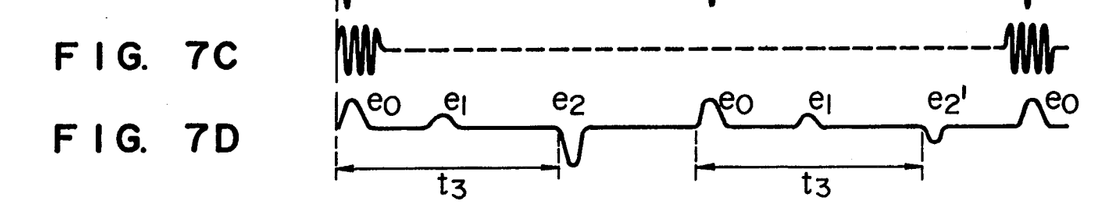

The technique in which the distance Li from the transducer unit surface P to the surface of the inspected object 24 shown in FIGS. 4B and 5A is calculated when the inspected object 24 is moved will be described with reference to FIGS. 7A through 7D. Initially, the ultrasonic wave beam is transmitted at a repetitive frequency T from the transducer unit 1 shown in FIG. 1 as shown in FIG. 7A. The echo signal reflected within the inspected object is received and converted into an electrical signal by the transducer unit 1 and processed by the ultrasonic wave transmission and reception unit 2, thereby being converted into reflection echo signals $E_0$, $E_1$, and $E_2$ corresponding to the depths as shown in FIG. 7B. Thereafter, the reflection echo signals $E_0$, $E_1$, and $E_2$ are phase-detected by the motion detector circuit 11 and then added with a reference wave (shown in FIG. 7C) synchronized with the above-mentioned repetitive frequency T, thereby Doppler frequency shift signals $e_0$, $e_1$, and $e_2$ being obtained as shown in FIG. 7D. At that time, although the amplitudes of the Doppler frequency shift signals $e_0$, and $e_1$ at the still portion are not changed, the amplitude of the Doppler frequency shift signal at the moving portion is changed at every cycle of the repetitive frequency T as in $e_2$ to $e_2'$.

Next, the Doppler frequency shift signal in which the moving portion of the inspected object is detected by the above-mentioned motion detector circuit 1 is input to the three-dimensional display processing circuit 13. At that time, the change of the portion ($e_2$, $e_2'$) affected by the Doppler effect appears in the Doppler frequency shift signal detected by the motion detector circuit 11 as the amplitude. Therefore, a time t3 required until a timing point at which the change of amplitude of arbitrary magnitude appears since the transducer unit 1 started receiving the reflection echo signal is obtained b the comparator 21 and the timer circuit 22 shown in FIG. 2. At that time, the comparator 21 compares the threshold value represented by the control signal G4 supplied thereto from the control circuit 7 shown in FIG. 1 and the Doppler frequency shift signal input thereto from the motion detector circuit 11. When the changed amount of the Doppler frequency shift signal input from the motion detector circuit 11 and the threshold value represented by the control signal G4 are coincident with each other or when the former becomes larger than the latter, then the comparator 21 supplies the control signal G7 to the succeeding timer circuit 22. The timer circuit 22 starts measuring the time under the control of the control signal G7 indicative of the reflection echo signal reception starting time from the control circuit 7 and ends measuring the time by the input of the control signal G7 from the comparator 21, thereby measuring the time t3 required until the change of the amplitude of the arbitrary magnitude appears since the transducer unit 1 started receiving the reflection echo signal. In this case, the above-mentioned time t3 represents a time up to the surface of the moving internal organ, and the distance Li from the transducer unit surface P to the surface of the inspected object 24 is calculated by velocity of sound within the living body x time t3 on the basis of the time t3 required till the change of the amplitude appears.

Thereafter, the signal representing the time t3 measured by the timer circuit 22 is input to the luminance conversion circuit 22 shown in FIG. 2, and thereby converted into an image display luminance value corresponding to the magnitude of the value of the time t3 calculated by using the conversion table memory provided within the luminance conversion circuit 23 and also digitized. This conversion table memory is the same as that used when the black and white image is displayed.

At that time, the Doppler frequency shift detector circuit 12 is supplied with the Doppler frequency shift signal output from the motion detector circuit 11 shown in FIG. 1 and detects whether the signal of the moving portion (e.g., bloodstream) within the inspected object represents the shift which approaches or goes away from the ultrasonic wave beam transmitting direction. Then, the Doppler frequency shift detector circuit 12 supplies the luminance conversion circuit 13 with a signal G9 that is used to display an image in different colors depending upon the approaching frequency shift and the going away frequency shift. In this case, the luminance conversion circuit 23 is a conversion table memory in which there are calculated corresponding relationship among the elapsed time calculated by the timer circuit 22, the color display signal G9 detected by the Doppler frequency shift detector circuit 12 and the luminance value.

Accordingly, the above-mentioned luminance conversion circuit 13 converts the signal into the image display luminance value corresponding to the magnitude of the value of the above calculated time t3 and also into the signal that is used to display the image in different colors depending on the frequency shift which approaches or goes away from the ultrasonic wave transmitting direction. From this, as shown in FIG. 8, the television monitor 6 can display an image with a brightness difference in accordance with the distance from the viewpoint in response to the shape of the inspected object 24 and also display a bloodstream component in different colors, for example, in red color when the frequency shift is the approaching frequency shift and in blue color when the shift frequency is the going away frequency shift. Therefore, the shape of the inspected object 24 can be observed as a three-dimensional image, and the moving direction of the moving portion can be definitely understood by different colors. Incidentally, in FIG. 1, the on- and off-state of the Doppler frequency shift detector circuit 12 can be switched by a control signal from the control circuit 7.

A three-dimensional display processing of the ultrasonic diagnostic apparatus according to the present invention will hereinafter be described with reference to flowcharts. These processings are controlled by the CPU in the control circuit 7.

Figure 9:
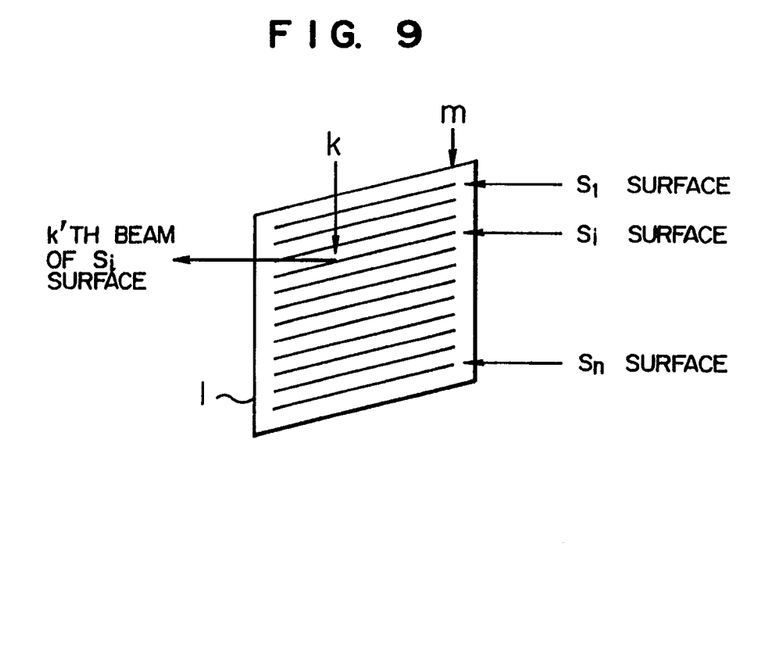
FIG. 9 is a diagram showing an order of transmitting ultrasonic beam for inspected body.

FIG. 9 is a diagram showing the manner that the ultrasonic wave beam is transmitted from the transducer unit 1.

Figure 10:
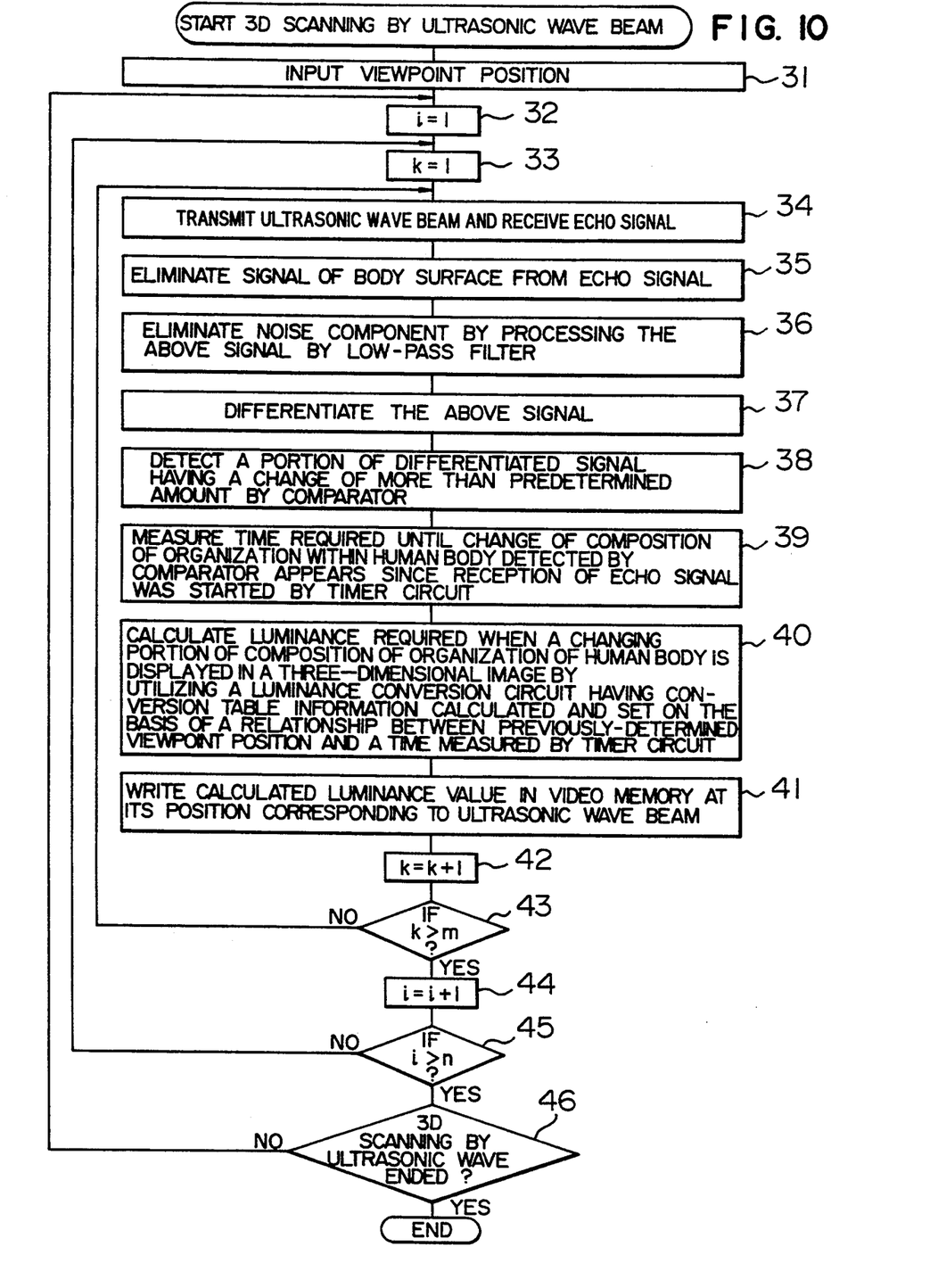
FIG. 10 is a flowchart to which reference will be made in explaining operation done when a black and white picture is displayed.

FIG. 10 is a flowchart for explaining operation that a black and white image is displayed in a three-dimensional display image.

As shown in FIG. 10, a viewpoint position is input at step 31. Then, the ultrasonic wave beam transmitting position is set to a first position of the scanning surface S1 at steps 32, 33. In the next step 34, the ultrasonic wave beam is transmitted and the echo signal is received. In the next step 35, the body surface portion signal is eliminated from the echo signal. In the next step 36, the signal from which the body surface portion signal is eliminated is supplied to the low-pass filter, in which the high-frequency noise thereof is reduced. In the next step 37, the signal with the noise reduced is differentiated. In the next step 38, the differentiated signal is detected at its portion having a change of larger than a predetermined magnitude by using the comparator. In the differentiated signal, the portion having the change of larger than the predetermined magnitude corresponds to the portion where the composition of the organization within the human body is changed. In the next step 39, a time required until the portion having the change of more than the predetermined magnitude is detected by the comparator since the echo signal has started being received is measured by the timer circuit. Since the echo signal is received immediately after the ultrasonic wave beam was transmitted, the time measured by the timer circuit is proportional to the distance from the body surface to the measurement point. In step 40, on the basis of the relationship between the previously-determined viewpoint position and the time measured by the timer circuit, the luminance value used when the measurement point, that is the changing point of the composition of the organization within the human body is displayed in a three-dimensional image is obtained by the luminance conversion circuit having the conversion table that was calculated and set in advance. In the next step 41, the luminance value thus obtained is written in the video memory at its position corresponding to the transmitted ultrasonic wave beam. Each time the ultrasonic wave beam transmitting point is displaced in the next steps 42 and 43, the processings from steps 34 to 41 are executed and the scanning in one scanning line is completed. When a series of operation in one scanning line is completed at steps 44 and 45, the scanning line is shifted one by one and all of the scanning is completed at step 46.

Figure 11:
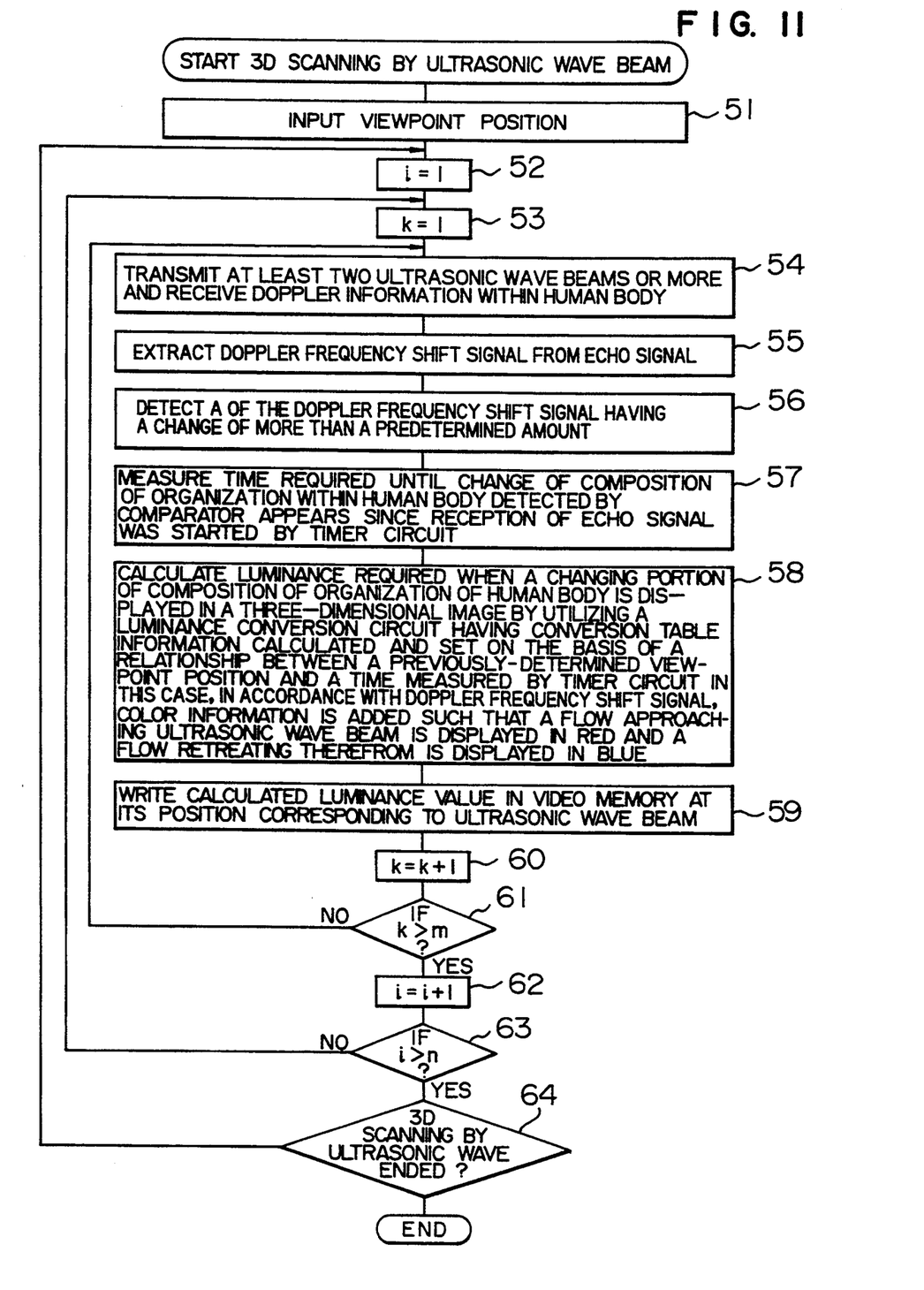
FIG. 11 is a flowchart to which reference will be made in explaining operation done when a color picture is displayed.

FIG. 11 is a flowchart used to display a color image in a three-dimensional display image.

As shown in FIG. 11, a viewpoint position is input at step 51. In steps 52 and 53, the ultrasonic wave beam transmitting position is set to the first position of the scanning surface S1. In the next step 54, at least two ultrasonic wave beams or more are transmitted and the echo signal containing the Doppler information within the human body is received. In the next step 55, the Doppler frequency shift signal is extracted from tile echo signal. In the next step 56, the Doppler frequency shift thus extracted is detected at its portion having a change larger than a predetermined magnitude by the comparator. This changed portion corresponds to the moving portion of the organization within the human body. In step 57, a time required until the portion having the change larger than the predetermined magnitude is detected by the comparator since the echo signal has started being received is measured by the timer circuit. In step 58, on the basis of the relationship between the previously-determined viewpoint position and the time measured by the timer circuit, the luminance value used when the measurement point that is the changing point of the composition of the organization within the human body is displayed in a three-dimensional image is obtained by the luminance conversion circuit having the conversion table that was calculated and set in advance. In this case, in accordance with the Doppler frequency shift information, color information is added such that the flow approaching the ultrasonic wave beam is displayed in red color and the flow that goes away from the ultrasonic wave beam is displayed in blue color. In step 59, the luminance value thus obtained is written in the video memory at its position corresponding to the transmitted ultrasonic wave beam. Each time the ultrasonic wave beam transmitting point is shifted once, the processings from steps 54 to 59 are executed and then the scanning on one scanning line is completed. When a series of processing at one scanning line is completed at steps 62 and 63, the scanning line is shifted one by one, and all scanning is completed at step 64.

What is claimed is:

1. An ultrasonic diagnostic apparatus comprising:
   means for transmitting an ultrasonic wave;
   means for receiving an echo signal reflected from an inspected object;
   means for detecting a portion which changes more than a predetermined magnitude in said received echo signal, said portion being a changing point corresponding to a measurement point to be measured within said inspected object;
   means for measuring an elapsed time until said changing point is detected from a timing point at which said echo signal is detected;
   means for obtaining luminance values in correspondence with said elapsed time as display luminance values of said measurement point; and
   means for displaying said measurement point within said inspected object by the luminance values thus obtained.

2. An ultrasonic diagnostic apparatus according to claim 1, wherein said means for obtaining luminance values includes means for calculating a distance from said ultrasonic wave transmitting means to said measurement point, a conversion table in which there is registered in advance a relationship among a viewpoint position, a distance to said measurement point and the luminance value, and means for obtaining a luminance value from said calculated distance and the input viewpoint position with reference to said conversion table.

3. An ultrasonic diagnostic apparatus according to claim 1, wherein said means for detecting said changing point includes means for comparing said echo signal obtained at every transmission of an ultrasonic wave beam with a threshold value of a predetermined magnitude.

4. An ultrasonic diagnostic apparatus according to claim 3, wherein said means for detecting said changing point includes means for eliminating a signal corresponding to a surface portion of said inspected object from said echo signal, a filter for reducing noise from a signal in which said signal corresponding to the surface portion of said inspected object is removed, means for obtaining a differentiated signal by differentiating an output of said filter, and means for comparing said differentiated signal with said threshold value.

5. An ultrasonic diagnostic apparatus according to claim 3, further comprising means for detecting whether a portion affected by said Doppler effect approaches or goes away from the ultrasonic wave beam transmitting direction, and means for displaying an approaching frequency shift and a retreating frequency shift in different colors.

6. An ultrasonic diagnostic apparatus according to claim 1, wherein said means for detecting said changing point includes means for extracting a Doppler frequency shift signal of an echo signal formed of at least more than two ultrasonic wave beams transmitted in the same direction, and means for comparing said Doppler frequency shift signal with a threshold value of a predetermined magnitude.

7. An ultrasonic diagnostic apparatus according to claim 4, wherein said means for detecting said changing point includes means for comparing said echo signal obtained at every transmission of one ultrasonic wave beam with a threshold value of a predetermined magnitude.

8. An ultrasonic diagnostic apparatus according to claim 7, wherein said means for detecting said changing point includes means for eliminating a signal corresponding to a surface portion of said inspected object from said echo signal, a filter for reducing noise from a signal in which said signal corresponding to the surface portion of said inspected object is removed, means for obtaining a differentiated signal by differentiating an output of said filter, and means for comparing said differentiated signal with said threshold value.

9. An ultrasonic diagnostic apparatus according to claim 7, further comprising means for detecting whether a portion affected by said Doppler effect approaches or goes away from the ultrasonic wave beam transmitting direction, and means for displaying an approaching frequency shift and a retreating frequency shift in different colors.

10. A display method in an ultrasonic diagnostic apparatus comprising the steps of:
    transmitting an ultrasonic wave beam;
    receiving an echo signal reflected from an inspected object;
    detecting a portion which changes more than a predetermined magnitude in said received echo signal, said portion being a changing point corresponding to a measurement point to be measured within said inspected object;
    measuring an elapsed time until said changing point is detected from a timing point at which said echo signal is detected;
    obtaining luminance values in correspondence with said elapsed time as display luminance values of said measurement point; and
    displaying said measurement point within said inspected object by the luminance values thus obtained.

11. A display method in an ultrasonic diagnostic apparatus according to claim 10, wherein said step for obtaining luminance values includes a step for calculating a distance from said ultrasonic wave transmitting means to said measurement point, a conversion table in which there is registered in advance a relationship among a viewpoint position, a distance to said measurement point and the luminance value, and a step for obtaining a luminance value from said calculated distance and the input viewpoint position with reference to a conversion table in which there is registered in advance a relationship among a viewpoint position, a distance to said measurement point and the luminance value.

12. A display method in an ultrasonic diagnostic apparatus according to claim 10, wherein said display step includes a step for writing a calculated luminance value in said video memory at its position corresponding to the transmitted ultrasonic wave beam.

13. A display method in an ultrasonic diagnostic apparatus according to claim 10, wherein said step for detecting said changing point includes a step for comparing said echo signal obtained at every transmission of an ultrasonic wave beam with a threshold value of a predetermined magnitude.

14. A display method in an ultrasonic diagnostic apparatus according to claim 10, wherein said step for transmitting said ultrasonic wave beam includes a step for transmitting at least two ultrasonic wave beams or more in the same direction, said step for detecting said changing point includes a step for extracting a Doppler frequency shift signal from the echo signal formed of at least two ultrasonic wave beams or more, and a step for comparing said Doppler frequency shift signal with said threshold value of the predetermined magnitude.

15. A display method in an ultrasonic diagnostic apparatus according to claim 14, wherein said step for extracting said Doppler signal includes a step for detecting whether a portion affected by said Doppler effect approaches or goes away from the ultrasonic wave beam transmitting direction, and said display step includes a step for displaying an approaching frequency shift and a retreating frequency shift in different colors.

16. A display apparatus in an ultrasonic diagnostic apparatus according to claim 10, wherein said step for detecting said changing point includes a step for eliminating a signal corresponding to a surface portion of said inspected object from said echo signal, a step for reducing noise from a signal in which said signal corresponding to the surface portion of said inspected object is removed by using a filter, a step for obtaining a differentiated signal by differentiating an output of said filter, and a step for comparing said differentiated signal with said threshold value.

* * * * *